(12) United States Patent
Schneider (10) Patent No.: US 11,340,311 B2
(45) Date of Patent: May 24, 2022

(54) DETERMINING POSITION AND ORIENTATION FROM A HELMHOLTZ DEVICE

(71) Applicant: Northern Digital Inc., Waterloo, CA (US)

(72) Inventor: Mark Robert Schneider, Williston, VT (US)

(73) Assignee: Northern Digital Inc., Waterloo, CA (US)

( * ) Notice: Subject to any disclaimer, the term of this patent is extended or adjusted under 35 U.S.C. 154(b) by 61 days.

(21) Appl. No.: 16/850,279

(22) Filed: Apr. 16, 2020

(65) Prior Publication Data

US 2020/0333404 A1 Oct. 22, 2020

Related U.S. Application Data

(60) Provisional application No. 62/834,721, filed on Apr. 16, 2019.

(51) Int. Cl.
*G01R 33/00* (2006.01)
*G01R 33/34* (2006.01)
(Continued)

(52) U.S. Cl.
CPC .......... *G01R 33/0017* (2013.01); *A61B 34/20* (2016.02); *G01R 33/34061* (2013.01); *G02B 27/017* (2013.01); *A61B 2034/2051* (2016.02)

(58) Field of Classification Search
CPC .... G01B 7/004; G01C 17/38; G01R 33/0035; G01R 33/0017; G01R 33/34061;
(Continued)

(56) References Cited

U.S. PATENT DOCUMENTS 4,109,199 A 8/1978 Ball et al.
4,623,842 A 11/1986 Bell et al.
(Continued)

FOREIGN PATENT DOCUMENTS

CA 2956893 2/2016
WO WO/2016022192 2/2016

OTHER PUBLICATIONS

CA Office Action in Canadian Appln. No. 3,078,012, dated Jun. 2, 2021, 6 pages.
(Continued)

*Primary Examiner* — Jermele M Hollington
*Assistant Examiner* — Taqi R Nasir
(74) *Attorney, Agent, or Firm* — Fish & Richardson P.C.

(57) ABSTRACT

A method includes receiving, at a magnetic sensor, a series of transmitter signals that are detected as a series of signals corresponding to different locations and/or orientations of a magnetic transmitter emitting a magnetic field, calculating, receiving, at the magnetic sensor, a measurement transmitter signal that is detected as a signal corresponding to a magnetic field provided by the magnetic transmitter, and calculating, based at least on the received measurement sensor signal and the calibration matrix, one or both of an orientation matrix indicative of an orientation of the magnetic sensor relative to the magnetic transmitter and a positional matrix indicative of a position of the magnetic sensor relative to the magnetic transmitter, wherein the series of transmitter signals are transmitted from the same physical location relative to the magnetic sensor.

21 Claims, 6 Drawing Sheets

(51) Int. Cl.
*A61B 34/20* (2016.01)
*G02B 27/01* (2006.01)

(58) Field of Classification Search
CPC ........ G06F 3/017; G06F 3/0346; G06F 3/012; A61B 34/20; A61B 2034/2051; G02B 27/017
See application file for complete search history.

(56) References Cited

U.S. PATENT DOCUMENTS

| | | | |
|---|---|---|---|
| 4,731,582 A | 3/1988 | Posseme et al. | |
| 5,126,669 A | 6/1992 | Honess et al. | |
| 5,307,072 A | 4/1994 | Jones, Jr. | |
| 5,672,967 A | 9/1997 | Jensen et al. | |
| 5,694,037 A | 12/1997 | Palstra et al. | |
| 6,130,534 A | 10/2000 | Huang et al. | |
| 6,242,907 B1 | 6/2001 | Clymer et al. | |
| 6,377,041 B1 | 4/2002 | Jones, Jr. et al. | |
| 6,456,069 B1 | 9/2002 | Scarzello et al. | |
| 6,624,626 B2 | 9/2003 | Khalfin | |
| 6,762,600 B2 | 7/2004 | Khalfin | |
| 7,259,550 B2 | 8/2007 | Bergsma | |
| 7,443,154 B1 * | 10/2008 | Merewether | G01V 3/08 324/67 |
| 7,719,261 B2 | 5/2010 | Geck et al. | |
| 7,759,941 B2 | 7/2010 | Bosnar | |
| 7,930,148 B1 * | 4/2011 | Figaro | G01C 17/38 702/196 |
| 8,963,538 B2 | 2/2015 | Jones et al. | |
| 2003/0184285 A1 * | 10/2003 | Anderson | A61B 5/06 324/207.17 |
| 2016/0041234 A1 | 2/2016 | Li et al. | |
| 2018/0088185 A1 * | 3/2018 | Woods | G06F 3/011 |

OTHER PUBLICATIONS

Kuipers, "Quaternions and Rotation Sequences," Geometry, Integrability and Quantization, Sep. 1-10, 1999, Varna, Bulgaria, pp. 127-143.

* cited by examiner

DETERMINING POSITION AND ORIENTATION FROM A HELMHOLTZ DEVICE

CLAIM OF PRIORITY

This application claims priority under 35 USC § 119(e) to U.S. Patent Application Ser. No. 62/834,721, filed on Apr. 16, 2019, the entire contents of which are hereby incorporated by reference.

TECHNICAL FIELD

This disclosure relates to determining position and orientation from a Helmholtz device.

BACKGROUND

Electromagnetic Tracking (EMT) systems are used to aid location of instruments and anatomy in medical procedures and in gaming applications. These systems utilize an electromagnetic transmitter in proximity to a magnetic sensor so that the sensor can be spatially located relative to the magnetic transmitter. Improper calibration of the sensor with respect to the transmitter can cause the EMT system to report incorrect sensor positions and orientations. This is usually detected and measured using some form of gantry system that precisely moves a sensor to known positions and orientations (P&O) with respect to the transmitter. Errors between the known P&O and those calculated by the EMT system are generally the only way to determine whether improper sensor calibration has occurred.

SUMMARY

Helmholtz coils are used to generate a uniform magnetic field over a certain volume in space between them. Each set of Helmholtz coils consists of two coils in an arrangement to maximize the spatial volume of uniform magnetic field. Three sets of Helmholtz coils arranged orthogonally can represent a 3 dimensional field. The magnetic field generated is proportional to a DC or AC current in the coils. These Helmholtz coils are typically used to calibrate a sensor, as is known in the art.

A calibration can be determined for the set of 3 Helmholtz coils. This calibration corrects for the misalignments of the Helmholtz coils and their gains, as is known in the art. Using this calibration, a Helmholtz system can be turned into a virtual transmitter (virtual transmitter and Helmholtz are used interchangeably herein). Rather than physically moving a sensor relative to a transmitter and measuring the resulting readings due to each new relative spatial position, the coil pairs of the described system virtually moves a sensor around with respect to a transmitter. That is, it generates the corresponding fields that a sensor would see if it were positioned and oriented at a desired pose with respect to an EMT system transmitter. This virtual motion eliminates the need for actual motion, such as is provided by a three-axis translation system. A sensor can be tested without ever moving the sensor from the middle of the Helmholtz coils that generate an experimental test field. A virtual transmitter is used without the need to modify the Helmholtz apparatus that was previously configured for calibrating the sensor, simplifying calibration and test.

In some aspects, a method includes receiving, at a magnetic sensor, a series of transmitter signals that are detected as a series of signals corresponding to different locations and/or orientations relative to the magnetic sensor of a magnetic transmitter emitting a magnetic field, and, calculating, based at least on the received measurement sensor signal and a Helmholtz calibration matrix, one or both of an orientation matrix indicative of an orientation of the magnetic sensor relative to the magnetic transmitter and a positional matrix indicative of a position of the magnetic sensor relative to the magnetic transmitter, wherein the series of transmitter signals are transmitted from the same physical location relative to the magnetic sensor. The magnetic sensor is typically a three-axis sensor that includes a concentric, collocated set of sensor coils, but could be one or two axes. The virtual magnetic transmitter is typically a three-axis virtual transmitter. Other configurations are possible and known in the art.

In some aspects, a computer-readable medium comprising instructions that when executed by a processor perform a method including receiving, at a magnetic sensor, a series of virtual transmitter signals that are detected as a series of signals corresponding to different locations and/or orientations relative to the magnetic sensor of a magnetic transmitter emitting a magnetic field, and calculating, based at least on the received measurement sensor signal and the calibration matrix, one or both of an orientation matrix indicative of an orientation of the magnetic sensor relative to the magnetic transmitter and a positional matrix indicative of a position of the magnetic sensor relative to the magnetic transmitter, wherein the series of transmitter signals are transmitted from the same physical location relative to the magnetic sensor.

In some aspects a system includes a magnetic transmitter configured to generate a magnetic field, a magnetic sensor configured to detect the generated magnetic field, and a computing device in communication with the magnetic transmitter and the magnetic sensor, the computing device configured to receive, at a magnetic sensor, a series of transmitter signals that are detected as a series of signals corresponding to different locations and/or orientations relative to the magnetic sensor of the magnetic transmitter emitting a magnetic field, and calculate, based at least on the received measurement sensor signal and the calibration matrix, one or both of an orientation matrix indicative of an orientation of the magnetic sensor relative to the magnetic transmitter and a positional matrix indicative of a position of the magnetic sensor relative to the magnetic transmitter, wherein the series of transmitter signals are transmitted from the same physical location relative to the magnetic sensor.

Advantages of the system described herein include using Helmholtz coils to both calibrate and test sensors in a single system. This simplification speeds up calibration and testing. The need for a three-axis translation system such as a gantry is eliminated.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

An Electromagnetic Tracking (EMT) system can be used in gaming and/or surgical settings to track devices (e.g., gaming controllers, head-mounted displays, medical equipment, robotic arms, etc.), thereby allowing their respective three-dimensional positions and orientations to be known to a user of the system. Augmented Reality (AR) and Virtual Reality (VR) systems also use EMT systems to perform head, hand, and body tracking, for example, to synchronize the user's movement with the AR/VR content. Such EMT systems use a magnetic transmitter in proximity to a magnetic sensor to determine the position and/or orientation of the sensor relative to the transmitter. Sensors used in such a system must provide accurate position and orientation information to the medical professional and are calibrated to ensure their accuracy. If an EMT sensor or transmitter is improperly calibrated, accuracy can be greatly diminished.

Sensor calibration can take place using conventional Helmholtz systems which mount a sensor in a Helmholtz coil, as is known in the art, or by using a three-axis (x, y, z) gantry that allows the position of the sensor or transmitter to be precisely known with respect to one another as it is moved around the experiment field. The transmitter emits signals that are detected by the sensor while the transmitter or the sensor is moved around the experiment field and data is collected. The resulting recorded data are run through one or more processes to produce a sensor calibration. To verify the correctness of this calibration, the gantry is once again used to move the sensor with respect to the transmitter while collecting data. The resulting recorded data are run through one or more processes that utilize the calibration and analyzed as to whether the position and orientation of the sensor with respect to the transmitter are correct as compared to the known gantry position and orientation (P&O).

Figure 1A:
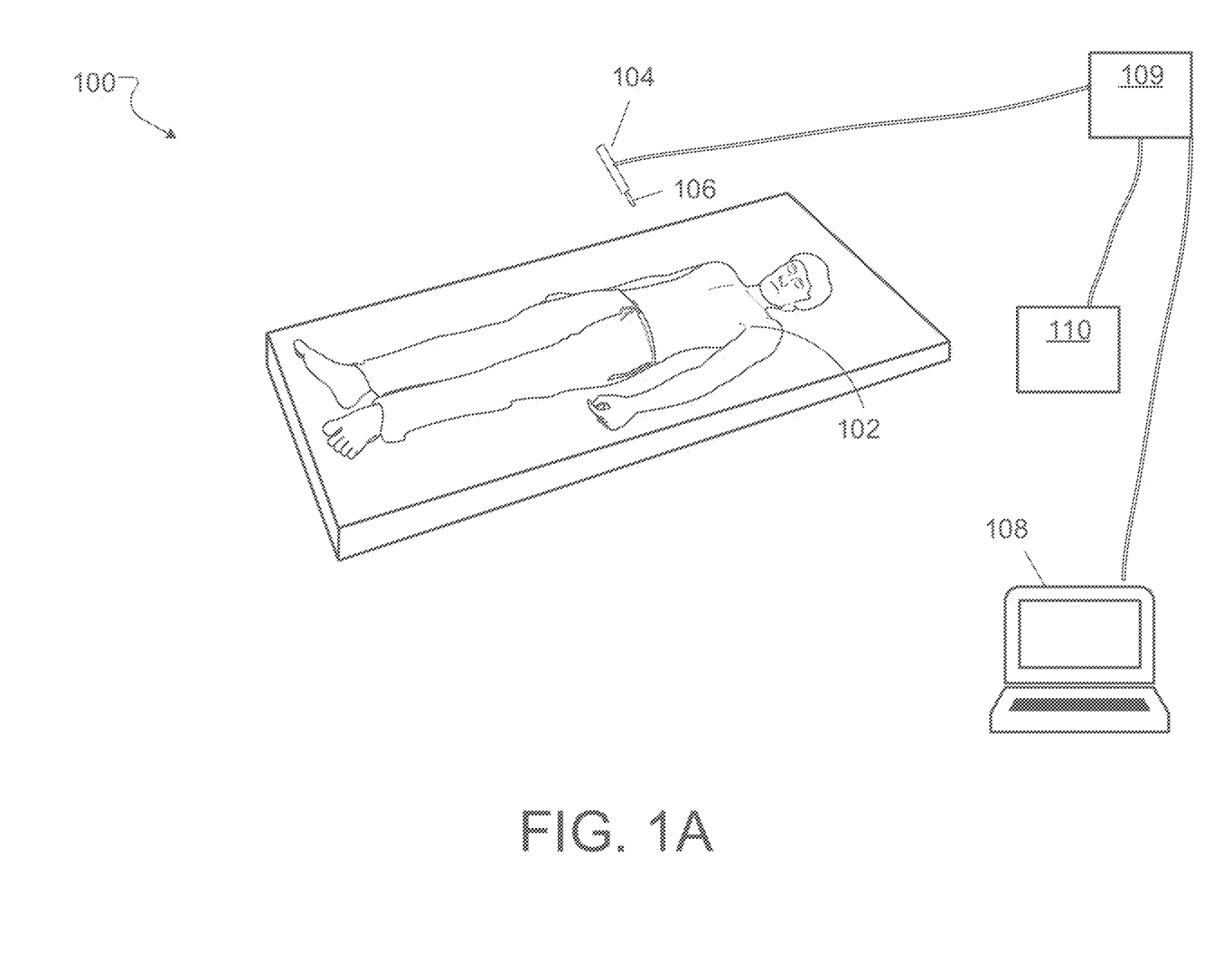
FIG. 1A is a schematic diagram of an Electromagnetic Tracking (EMT) system that includes a magnetic sensor and a magnetic transmitter.

FIG. 1A is an exemplary embodiment of the EMT system 100, which can be used for image-guided medical procedures performed on a patient 102, for example. The system 100 may include a freely moving medical instrument 104, which can include any manner of surgical tools and devices for use in medical treatment. The system 100 permits targeting of an anatomical organ, structure, vessel, etc. for visualization, diagnostic, interventional purposes, etc.

Instruments for use in the EMT system 100 may include one or more magnetic sensors including one or more coils. For example, the instrument 104 may include a three-axis sensor 106 that includes a concentric, collocated set of sensors coils. The sensor 106 may be embedded in a channel, affixed to a tip, etc., of the instrument 104. The particular sensor employed by the system 100 may be determined by the procedure type and/or the measurement performance requirements. The sensor 106 is connected to an electronic unit 109 and a computing device (e.g., a computer 108), etc. via a wired or wireless connection.

Under control of circuitry for energizing magnetic fields, the sensor 106 measures the fields, which are then processed by electronics unit 109 and its instantaneous position (x, y, z) and orientation angles (azimuth, altitude, roll) in three-dimensional space referenced to a transmitter 110's magnetic fields are calculated in computing device 108. Like the sensor 106, the particular transmitter employed by the system 100 may be determined by the procedure type, measurement performance requirements, etc. In some implementations, the transmitter 110 may be a three-axis transmitter that includes a concentric, collocated set of transmitter coils. The transmitter 110 is typically fixed in space besides, above, or beneath the patient or on medical equipment, where it acts as a spatial reference frame for the measurements provided by the sensor 106.

In some implementations, the computer 108 is an imaging computer that is configured to provide imaging capabilities to the system 100. The imaging computer 108, which can be in wired or wireless communication with the sensor 106 and transmitter 110, is configured to store pre-acquired or intra-operative images of the patient 102 in an image database. Such images may then be input to imaging software for registration and visualization purposes. During the medical procedure, the three-dimensional location of the instrument 104 can be tracked relative to the anatomy of the patient 102 and the pre-acquired or inter-operative images are presented in real time on a display of the computer 108. When the instrument 104 advances toward the target of interest within the body of the patient 102, the transmitter 110 can be activated and energized, thus producing electromagnetic signals that are sensed by the sensor 106 and represented as signals (e.g., voltage signals). These signals are processed in electronics unit 109 and the three-dimensional location is computed by computer 108. In some implementations, the computer 108 includes a guidance electronics unit 109 that is configured to process the voltage signals in order to provide the three-dimensional location.

Figure 1B:
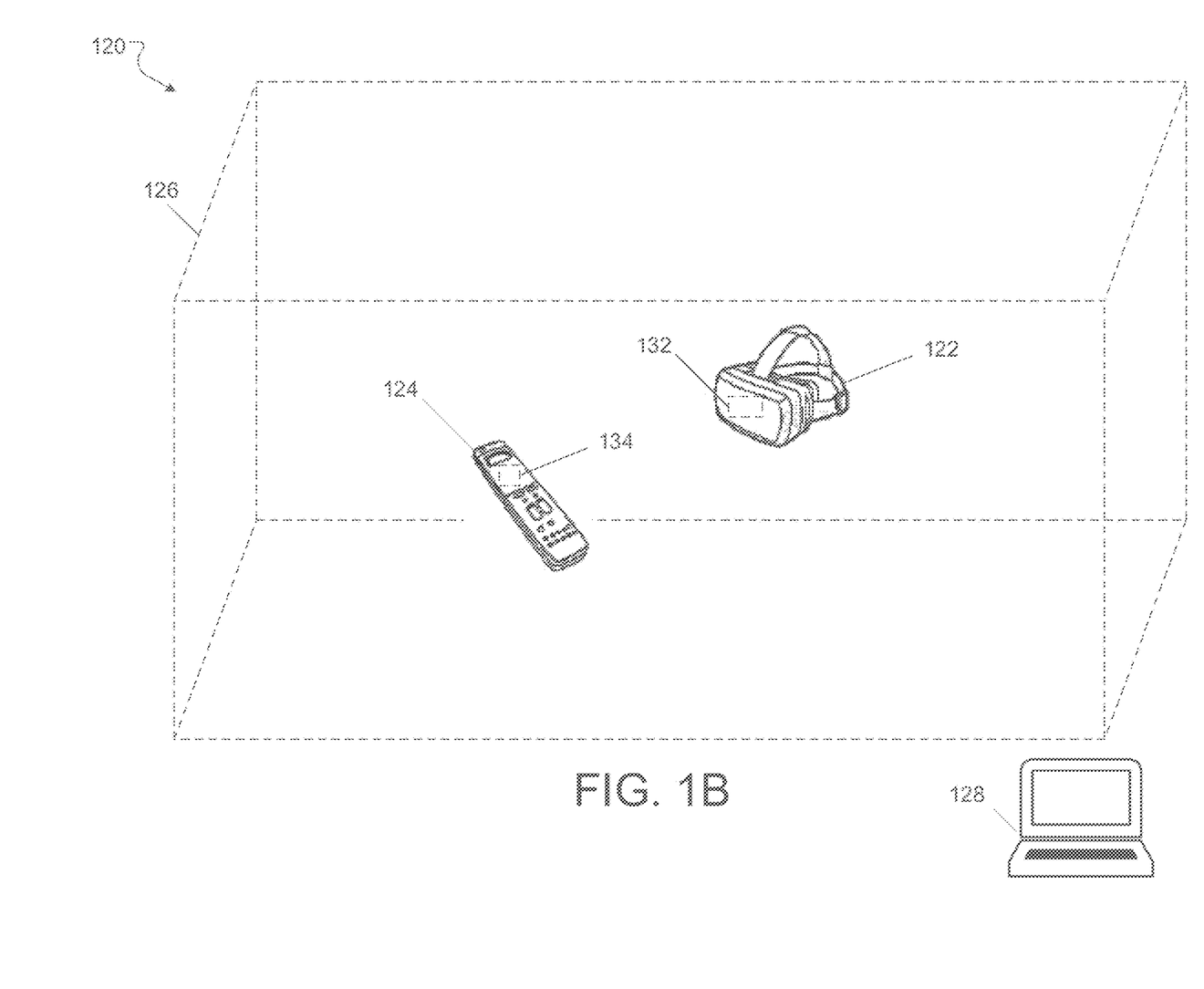
FIG. 1B is a schematic diagram of another example EMT system that includes a magnetic sensor and a magnetic transmitter.

FIG. 1B shows another example of an EMT system 120 that can be used as part of a VR/AR or other system (e.g., a medical system such as in FIG. 1A, or a gaming system). The EMT system 120 includes at least a head-mounted display (HMD) 122 that includes a magnetic sensor 132 along with processing and computation resources and a controller 124 that includes a magnetic transmitter 134 along with processing and computation resources, as required. The HMD 122 and the controller 124 are configured to track position and orientation in three-dimensional space relative to each other. For example, the EMT transmitter 134 of the controller 124 is configured to track the sensor 132 of the HMD 122 relative to a reference frame defined by the position and orientation of the transmitter 134, or the EMT sensor 132 of the HMD 122 is configured to track the transmitter 134 of the controller 124 relative to a reference frame defined by the position and orientation of the sensor 132. The particular sensor 132 and transmitter 134 employed by the EMT system 120 may be determined by the process for which it is being used, measurement performance requirements, etc.

The position and orientation of the HMD 122 and the controller 124 can be tracked relative to each other within a tracking volume 126. While the tracking volume 126 is illustrated as being a defined space, it should be understood that the tracking volume 126 may be any three-dimensional space, including dimensionless three-dimensional spaces (e.g., large indoor and/or outdoor areas, etc.).

In some implementations, the transmitter 110 or 134 includes three orthogonally wound magnetic coils, referred to herein as the x, y, and z coils. Electrical currents traveling through the three coils cause the coils to produce three orthogonal magnetic fields at three frequencies (e.g., three different frequencies) for FDM (frequency division multiplexing) applications or three pulses (e.g., three different time slots) for TDM (time division multiplexing) applications. The three frequencies may be three closely spaced frequencies, e.g., 34 KHz, 34.25 KHz, and 34.5 KHz, although other frequencies can also or alternatively be used. In some implementations, the coils may produce magnetic fields at the same frequency as, for example, used in a TDM fashion. The sensor 106 or 132 also includes three orthogonally wound magnetic coils, referred to herein as the x, y, and z coils. Voltages are induced in the coils of the sensor 106 or 132 in response to the transmitter 110 or 134 generated magnetic fields by means of magnetic induction. Each coil of the sensor 106 or 132 generates an electrical signal for each of the magnetic fields generated by the coils of the transmitter 110 or 134; for example, the x coil of the sensor 104 or 132 generates a first electrical signal in response to the magnetic field received from the x, y and z coil of the transmitter 110 or 134 They and z coils of the sensor 110 or 132 similarly generate electrical signals for each of the magnetic fields received from each coil of the transmitter 110 or 134. The sensor may also be constructed of other sensing elements that measure magnetic fields, e.g., Hall effect elements, etc. In other cases, transmitter 110 may have many more coils than 3 and the sensor 106 may have less than 3, with the number of sensor coils times the number of transmitter coils being a value greater than or equal to 6.

The data from the sensor 132 can be represented as a matrix of data (e.g., a 3×3 matrix), which can be resolved into the position and orientation of the sensor 104 or 132 with respect to the transmitter 110 or 134, or vice versa. In particular, electronics incorporated into the HMD 122 are configured to determine the position and orientation of the controller 124 relative to the HMD 122 based on the characteristics of the magnetic fields generated by the transmitter 134 and the various electrical signals measured at the sensor 132. As described above, a computer system 128 may also be configured to determine the position and orientation of a sensor and/or a transmitter.

In some implementations, before the start of the procedure using the EMT system 100 or 120, one or more protocols are implemented. One protocol may initialize the instrument 104 and sensor 106, or the sensor 132, to prepare for tracking by the computer 108 or 208. Configuration data, such as instrument type, part number, sensor location in the instrument, calibration data, etc. may be stored in a memory of the computer 108 or 208. The position and orientation of the sensor 106 or 132 with respect to the transmitter 134 or 110 must be finely calibrated before initialization of the instrument begins, as precise and accurate calibration is desirable for accurate readings of the instrument. Calibration of the sensor is desirable since the windings that make up the coils of the sensor may not be exact and may deviate from theoretical (e.g., the number of windings present on the instrument coils varies from ideal, the spacing of the turns isn't exact, or diameter, shape, etc. of the wound coils are/is not precise). If the transmitter 134 and/or the sensor 132 is not calibrated accurately (FIG. 1A), or the three-axis sensor 106 and/or transmitter 110 is not calibrated accurately (FIG. 1B), the determined (e.g., calculated) position and orientation of the transmitter 134 or transmitter 100 and/or sensor 132 or three-axis sensor 106 may not reflect the true (e.g., actual) position and orientation.

Determining Virtual Orientation and Position of the Sensor

Figure 2:
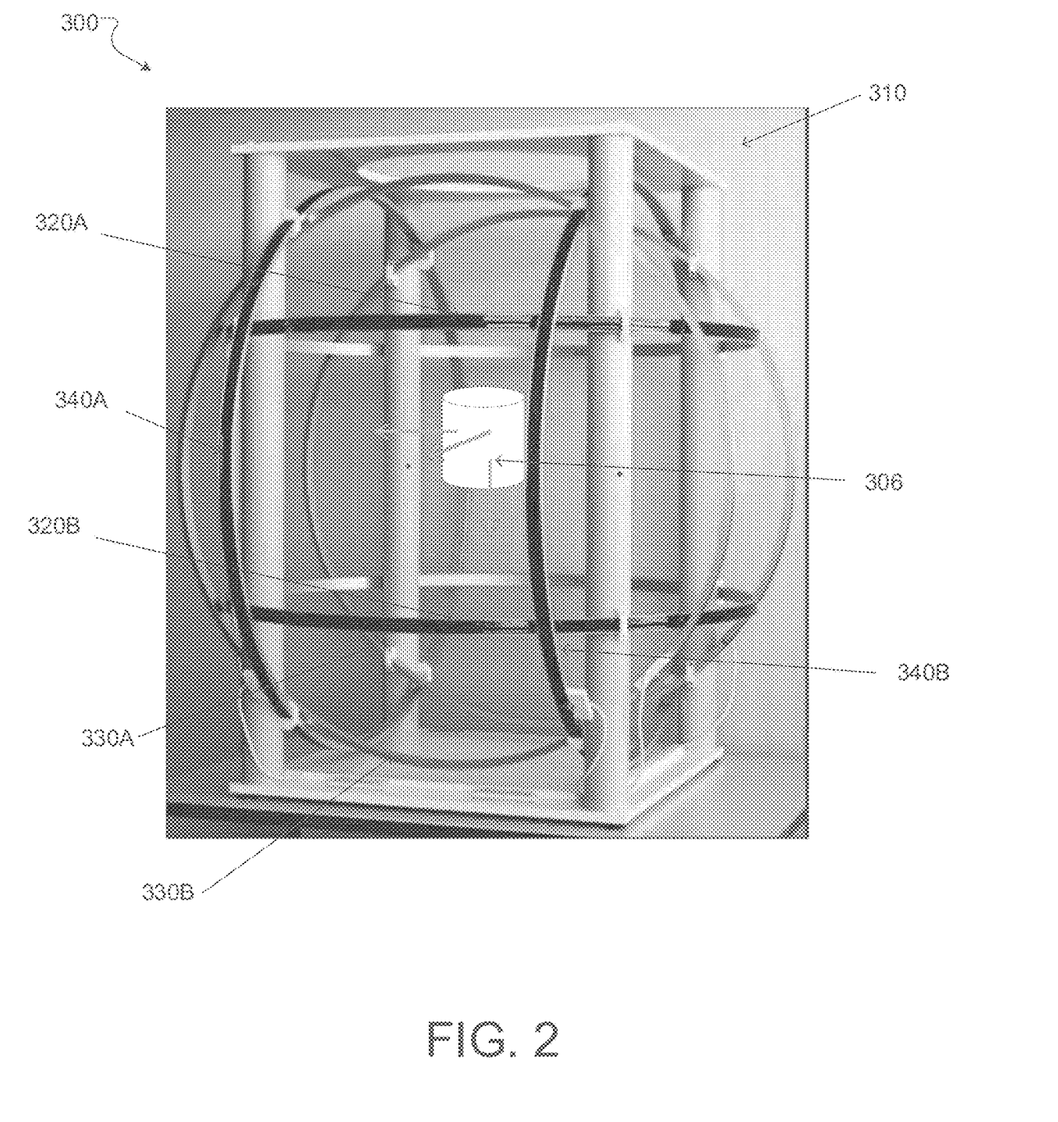
FIG. 2 is a schematic of a Helmholtz system for steering a magnetic sensor.

A method is set out below that can be used to validate a magnetic tracking system such as system 300 that has three orthogonal axes transmitters/sensors such as shown in FIG. 2. One needs to calculate a Helmholtz calibration matrix H, describing mathematically the characteristics of the Helmholtz coils, as is known in the art. The system 300 generates a transmitter signal that is detected at the sensor 306 as a virtual signal corresponding to a magnetic field provided by magnetic transmitter 110 or 134. Using the calibration matrix, the system 300 uses this received signal to calculate the apparent orientation and position of the sensor 306 relative to the virtual transmitter 310. This calculation can include determining a matrix indicative of orientation and a positional matrix, corresponding to three orientation indicator values (azimuth, altitude, roll) and three positional indicator values (x, y, z).

The following material is from "Quaternions and Rotation Sequences," by J. B. Kuipers and is incorporated by reference. Three Helmholtz coil sets including coils 320A, 320B, 330A, 330B, 340A, 340B are driven to produce the equivalent of a dipole field. The ratio of the excitation of the coils is k*C, where C is the diagonal matrix with elements [1, −½, −½] for this to occur. Controlling the strength of k allows one to control the apparent distance between the sensor 306 under test (which is itself a three-coil sensor, e.g., sensor 306) and the virtual transmitter 310 created by the Helmholtz. Allowing the three Helmholtz coil pairs of coils 320A, 320B, 330A, 330B, 340A, 340B to be energized in a frequency division or time division multiplexing manner and at different excitations enables the virtual movement of the sensor 306.

The energization pattern to achieve a virtual transmitter can be constructed by applying the following formula:

$$S = \frac{k}{r^3} AP^t CP \qquad (1)$$

Where S is the 3×3 signal matrix, k is a constant that sets the range, r is the range, A is the 3×3 direction cosine matrix (the orientation of the sensor), C is the coupling matrix and P is the position matrix in spherical coordinates (α, β, r) if measuring sensor position with respect to the transmitter.

A is defined as:

$$A = \begin{bmatrix} ca\ ce & sa\ ce & -se \\ ca\ se\ sr - sa\ cr & sa\ se\ sr + ca\ cr & ce\ sr \\ ca\ se\ sr + sa\ sc & sa\ se\ cr + ca\ sr & ce\ cr \end{bmatrix} \qquad (2)$$

Where ca is cos(azimuth), sa is sin(azimuth), ce is cos(elevation), se is sin(elevation), cr is cos(roll) and sr is sin(roll). P is defined as $$P = \begin{bmatrix} ca\ c\beta & sa\ c\beta & -s\beta \\ -sa & ca & 0 \\ ca\ s\beta & sa\ s\beta & c\beta \end{bmatrix} \qquad (3)$$

Where cα is cos(alpha), sα is sin(alpha), cβ is cos(beta) and sβ is sin(beta). In turn, the following trigonometric identities apply:

$$r^2=x^2+y^2+z^2 \quad w^2=x^2+y^2=r^2-z^2$$

$$c\alpha=x/w \quad s\alpha=y/w \quad c\beta=w/r \quad s\beta=-z/r \quad (4)$$

C, the coupling matrix, describes the near field electromagnetic coupling of coaxial and coplanar coils (e.g., the x direction coils of the sensor face the x direction coil coils of the transmitter). It is defined as:

$$C = \begin{bmatrix} 1 & 0 & 0 \\ 0 & -1/2 & 0 \\ 0 & 0 & -1/2 \end{bmatrix} \quad (5)$$

Calibration for Accurate Determination of Sensor Orientation and Position

Helmholtz calibration yields a 3×3 characterization matrix H. This is applied, along with the sensor characterization matrix SGO that is calculated from a sensor calibration as follows:

$$SGO \cdot S \cdot H = \frac{k}{r^3} AP^t CP \quad (6)$$

SGO·S produces an ideal sensor response. The determination of k is accomplished by setting the Helmholtz excitations, collecting the voltages from the sensor and multiplying the voltages by a single value k until the algorithm produces, for example, x, y, z=[8,0,0]. While watching the received sensor signals, turn on the Helmholtz coils one at a time (for a TDM implementation). Note the value of the Helmholtz x coil excitation, call this Bx. Adjust the y and z Helmholtz coil excitations so that they are half their present amplitude and the phase is reversed (180 degree phase shift) or the amplitude negated, and store the excitation as By and Bz, respectively. Then, connect the calibrated sensor and collect the voltages across the sensor coils. This forms the S matrix. One can collect one column of S at a time and form a full 3×3 matrix S, as would happen with a TDM implementation Then, form SGO*S*H which has the form:

$$\begin{bmatrix} V & 0 & 0 \\ 0 & -V/2 & 0 \\ 0 & 0 & -V/2 \end{bmatrix} \quad (7)$$

Where V is a constant.

Then, solve for k in equation (6), by setting r (=8 inches in this example), A=P=3×3 identity matrix, and k is the value that makes the left-hand side equal the right hand side (in a least squares sense). That is:

$$SGO \cdot S \cdot H - \frac{k}{r^3} AP^t CP \cong 0 \quad (8)$$

or, making the substitutions $$\begin{bmatrix} V & 0 & 0 \\ 0 & -V/2 & 0 \\ 0 & 0 & -V/2 \end{bmatrix} - \frac{k}{8^3} \begin{bmatrix} 1 & 0 & 0 \\ 0 & -1/2 & 0 \\ 0 & 0 & -1/2 \end{bmatrix} \cong 0 \quad (8a)$$

Once k is determined, any sensor can be virtually moved with respect to the transmitter. Working in reverse, enter the desired position into equation (4). Form the desired P matrix from equation (3). Enter the desired orientation into equation (2). Then form the following using the determined k and the sensor SGO:

$$S_{virtual} = \frac{k}{r^3} SGO^{-1} AP^t CPH^{-1} \quad (9)$$

Calculate the RSS (root sum squares value of each column of $S_{virtual}$, labelled Sv1, Sv2 and Sv3, respectively. Then multiply Sv1 by Bx, Sv2 by By and Sv3 by Bz to form Ex, Ey and Ez, respectively. Adjust the x, y and z coil Helmholtz excitations to Ex, Ey and Ez, respectively.

The resulting position and orientation output by the system should match the position and orientation information input initially. If this is the case, or within an acceptable amount of error (e.g., deviation of less than 1 mm in position and less than 0.2 degrees), the calibration has been proven successful. The calibrated sensor 306 can be tested by virtually moving the transmitter 310 around to ensure the sensor 306 responds as expected to the signals of the virtual transmitter. This testing of the sensor 306 can be done on the same Helmholtz system that it was calibrated on, for example, without the need to remove the sensor 306 from the Helmholtz.

The system 300 can also alert a user that a sensor that is being calibrated with the system 300 is defective. For example, if the steps outlined above are followed, in some instances the calibration parameters determined are outside of predetermined tolerance values. Since virtual movements of the transmitter 310 would result in inaccurate position and orientation readings the system 300 may alert the user that the sensor has failed to reach an acceptable calibration standard.

Figure 3:
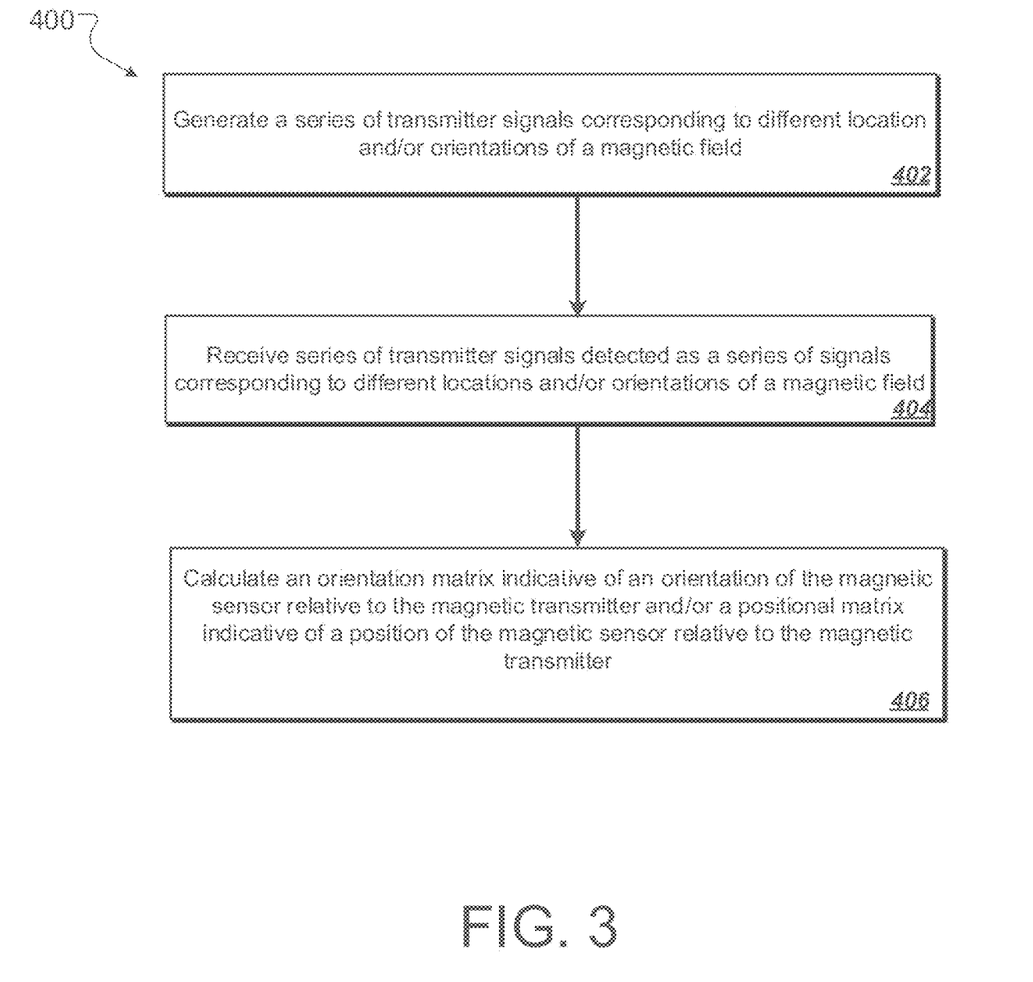
FIG. 3 is flow chart showing a method for steering the magnetic field from a Helmholtz to create a virtual transmitter and determining the position and orientation of the sensor with respect to the virtual transmitter.

Referring to FIG. 3, a method 400 of steering a sensor 306 with respect to a virtual transmitter 310 is outlined. At step 420 the system generates the magnetic fields corresponding to a particular position and orientation of the sensor 306 with respect to the virtual transmitter 310. At step 404 the system receives, at a magnetic sensor, a series of transmitter signals that are detected as a series of signals corresponding to different location and/or orientations of a magnetic field provided by a magnetic transmitter relative to the magnetic sensor. At step 406, the system calculates, based at least on the received sensor signal and the sensor and Helmholtz calibration matrices, one or both of an orientation matrix indicative of an orientation of the magnetic sensor relative to the magnetic transmitter and a positional matrix indicative of a position of the magnetic sensor relative to the magnetic transmitter. For example, this can include calculating equations (8) and (9) as described above.

In the above steps the series of transmitter signals are transmitted from the transmitter 310 which acts as a virtual transmitter virtually moving around the magnetic sensor 306 while actually remaining in the same physical location relative to the magnetic sensor 306.

Figure 4:
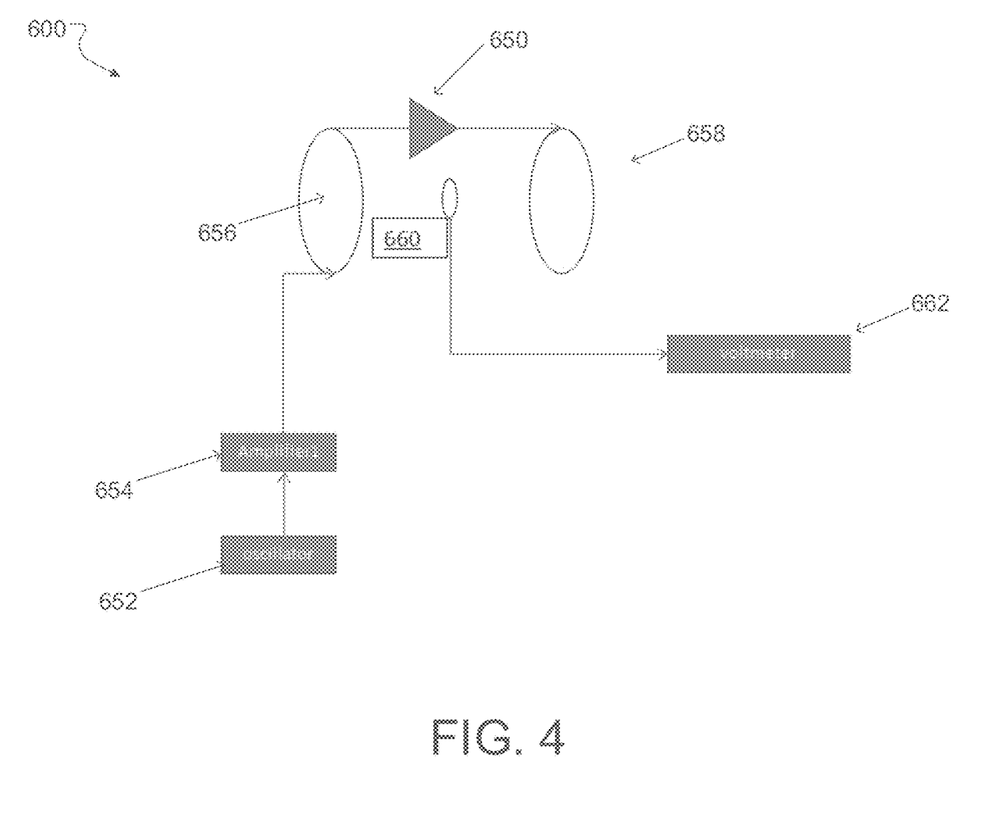
FIG. 4 is a schematic representation of a Helmholtz coil set used for uniform field generation.

Referring to FIG. 4, a control schematic 600 for controlling one axis of a Helmholtz coil set is shown (e.g., one of the coil pairs of system 300). A first amplifier 650 can be a unity gain, inverting, adjustable amplifier or just a straight through connection. An oscillator 652 produces an AC or pulsed DC signal. It is amplified by a second amplifier 654, which drives the Helmholtz coil 656 (e.g., one of the coils of system 300). The second Helmholtz coil 658 (e.g., another of the coils of system 300) is driven either in phase or out of phase depending on the configuration of the first amplifier 650. The Helmholtz coils 656, 658 induce a voltage at one of the sensor coils 660 (only one coil shown for convenience), which is measured by a voltmeter 662 or similar instrument. A similar control schematic can be used for each pair of coils on a three-axis Helmholtz set with a three-axis sensor so as to fully characterize the sensor 660.

Figure 5:
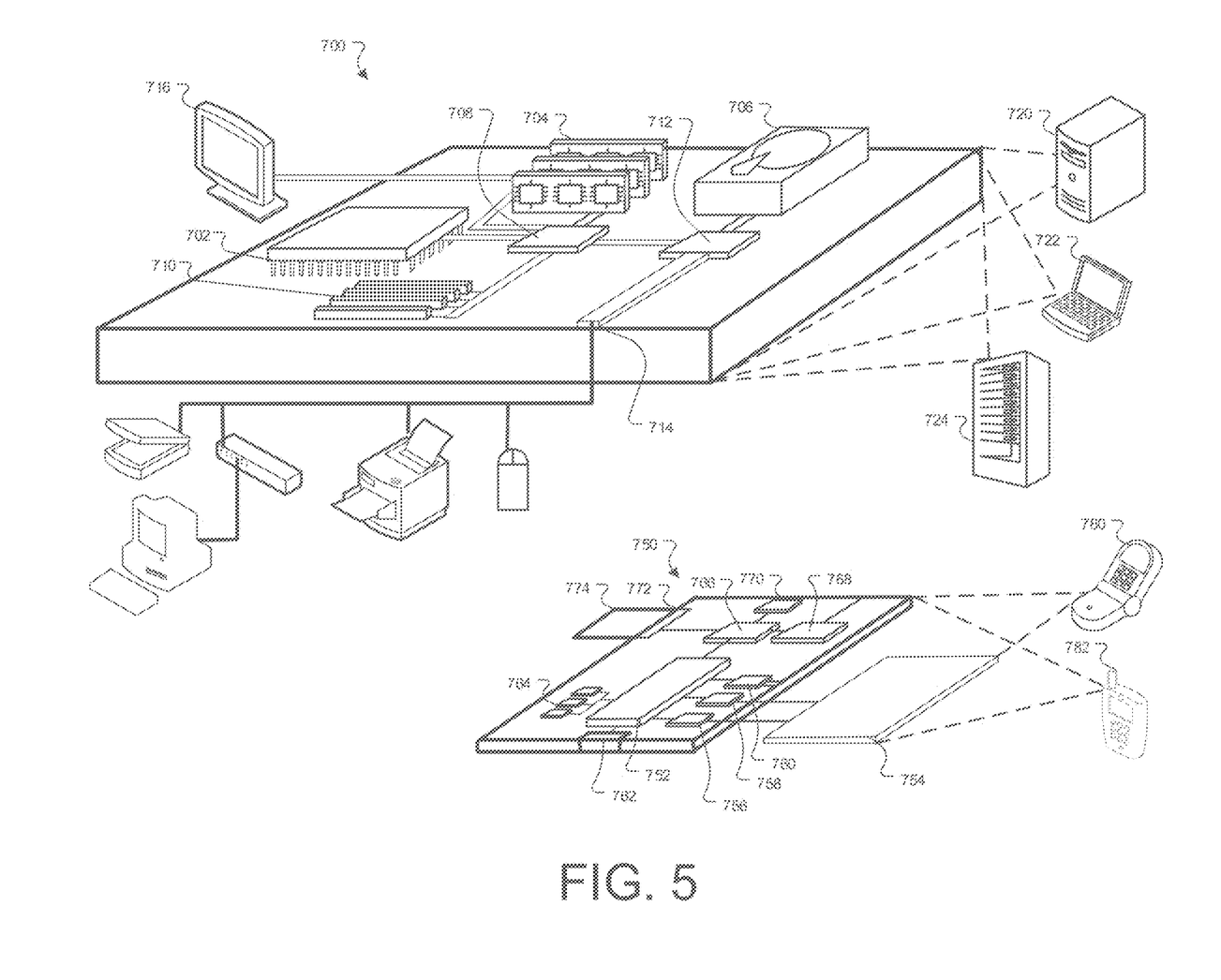
FIG. 5 illustrates an example of a computing device and a mobile computing device that can be used to implement the techniques described here.

The EMT calibration technique described above can be implemented using software included on a computer-readable medium for execution on a computer (e.g., the computer 108 of FIG. 1). FIG. 5 shows an example computer device 700 and example mobile computer device 750, which can be used to implement the techniques described herein. For example, a portion or all of the operations of a processor (e.g., the computer 108 shown in FIG. 1) may be executed by the computer device 700 and/or the mobile computer device 750. Computing device 700 is intended to represent various forms of digital computers, including, e.g., laptops, desktops, workstations, personal digital assistants, servers, blade servers, mainframes, and other appropriate computers. Computing device 750 is intended to represent various forms of mobile devices, including, e.g., personal digital assistants, cellular telephones, smartphones, and other similar computing devices. The components shown here, their connections and relationships, and their functions, are meant to be examples only, and are not meant to limit implementations of the techniques described and/or claimed in this document.

Computing device 700 includes processor 702, memory 704, storage device 706, high-speed interface 708 connecting to memory 704 and high-speed expansion ports 710, and low speed interface 712 connecting to low speed bus 714 and storage device 706. Each of components 702, 704, 706, 708, 710, and 712, are interconnected using various busses, and can be mounted on a common motherboard or in other manners as appropriate. Processor 702 can process instructions for execution within computing device 700, including instructions stored in memory 704 or on storage device 706, to display graphical data for a GUI on an external input/output device, including, e.g., display 716 coupled to high speed interface 708. In other implementations, multiple processors and/or multiple buses can be used, as appropriate, along with multiple memories and types of memory. Also, multiple computing devices 700 can be connected, with each device providing portions of the necessary operations (e.g., as a server bank, a group of blade servers, or a multi-processor system).

Memory 704 stores data within computing device 700. In one implementation, memory 704 is a volatile memory unit or units. In another implementation, memory 704 is a non-volatile memory unit or units. Memory 704 also can be another form of computer-readable medium, including, e.g., a magnetic or optical disk.

Storage device 706 is capable of providing mass storage for computing device 700. In one implementation, storage device 706 can be or contain a computer-readable medium, including, e.g., a floppy disk device, a hard disk device, an optical disk device, a tape device, a flash memory or other similar solid state memory device, or an array of devices, including devices in a storage area network or other configurations. A computer program product can be tangibly embodied in a data carrier. The computer program product also can contain instructions that, when executed, perform one or more methods, including, e.g., those described above. The data carrier is a computer- or machine-readable medium, including, e.g., memory 704, storage device 706, memory on processor 702, and the like.

High-speed controller 708 manages bandwidth-intensive operations for computing device 700, while low speed controller 712 manages lower bandwidth-intensive operations. Such allocation of functions is an example only. In one implementation, high-speed controller 708 is coupled to memory 704, display 716 (e.g., through a graphics processor or accelerator), and to high-speed expansion ports 710, which can accept various expansion cards (not shown). In the implementation, the low-speed controller 712 is coupled to storage device 706 and low-speed expansion port 714. The low-speed expansion port, which can include various communication ports (e.g., USB, Bluetooth®, Ethernet, wireless Ethernet), can be coupled to one or more input/output devices, including, e.g., a keyboard, a pointing device, a scanner, or a networking device including, e.g., a switch or router (e.g., through a network adapter).

Computing device 700 can be implemented in a number of different forms, as shown in the figure. For example, it can be implemented as standard server 720, or multiple times in a group of such servers. It also can be implemented as part of rack server system 724. In addition or as an alternative, it can be implemented in a personal computer (e.g., laptop computer 722). In some examples, components from computing device 700 can be combined with other components in a mobile device (not shown) (e.g., device 750). Each of such devices can contain one or more of computing device 700, 750, and an entire system can be made up of multiple computing devices 700, 750 communicating with each other.

Computing device 750 includes processor 752, memory 764, and an input/output device including, e.g., display 754, communication interface 766, and transceiver 768, among other components. Device 750 also can be provided with a storage device, including, e.g., a microdrive or other device, to provide additional storage. Components 750, 752, 764, 754, 766, and 768, may each be interconnected using various buses, and several of the components can be mounted on a common motherboard or in other manners as appropriate.

Processor 752 can execute instructions within computing device 750, including instructions stored in memory 764. The processor can be implemented as a chipset of chips that include separate and multiple analog and digital processors. The processor can provide, for example, for the coordination of the other components of device 750, including, e.g., control of user interfaces, applications run by device 750, and wireless communication by device 750.

Processor 752 can communicate with a user through control interface 758 and display interface 756 coupled to display 754. Display 754 can be, for example, a TFT LCD (Thin-Film-Transistor Liquid Crystal Display) or an OLED (Organic Light Emitting Diode) display, or other appropriate display technology. Display interface 756 can comprise appropriate circuitry for driving display 754 to present graphical and other data to a user. Control interface 758 can receive commands from a user and convert them for submission to processor 752. In addition, external interface 762 can communicate with processor 642, so as to enable near area communication of device 750 with other devices. External interface 762 can provide, for example, for wired communication in some implementations, or for wireless communication in other implementations. Multiple interfaces also can be used.

Memory 764 stores data within computing device 750. Memory 764 can be implemented as one or more of a computer-readable medium or media, a volatile memory unit or units, or a non-volatile memory unit or units. Expansion memory 774 also can be provided and connected to device 850 through expansion interface 772, which can include, for example, a SIMM (Single In Line Memory Module) card interface. Such expansion memory 774 can provide extra storage space for device 750, and/or may store applications or other data for device 750. Specifically, expansion memory 774 can also include instructions to carry out or supplement the processes described above and can include secure data. Thus, for example, expansion memory 774 can be provided as a security module for device 750 and can be programmed with instructions that permit secure use of device 750. In addition, secure applications can be provided through the SIMM cards, along with additional data, including, e.g., placing identifying data on the SIMM card in a non-hackable manner.

The memory can include, for example, flash memory and/or NVRAM memory, as discussed below. In one implementation, a computer program product is tangibly embodied in a data carrier. The computer program product contains instructions that, when executed, perform one or more methods, including, e.g., those described above. The data carrier is a computer- or machine-readable medium, including, e.g., memory 764, expansion memory 774, and/or memory on processor 752, which can be received, for example, over transceiver 768 or external interface 762.

Device 750 can communicate wirelessly through communication interface 766, which can include digital signal processing circuitry where necessary. Communication interface 766 can provide for communications under various modes or protocols, including, e.g., GSM voice calls, SMS, EMS, or MMS messaging, CDMA, TDMA, PDC, WCDMA, CDMA2000, or GPRS, among others. Such communication can occur, for example, through radio-frequency transceiver 768. In addition, short-range communication can occur, including, e.g., using a Bluetooth®, WiFi, or other such transceiver (not shown). In addition, GPS (Global Positioning System) receiver module 770 can provide additional navigation- and location-related wireless data to device 750, which can be used as appropriate by applications running on device 750.

Device 750 also can communicate audibly using audio codec 760, which can receive spoken data from a user and convert it to usable digital data. Audio codec 760 can likewise generate audible sound for a user, including, e.g., through a speaker, e.g., in a handset of device 750. Such sound can include sound from voice telephone calls, recorded sound (e.g., voice messages, music files, and the like) and also sound generated by applications operating on device 750.

Computing device 750 can be implemented in a number of different forms, as shown in the figure. For example, it can be implemented as cellular telephone 780. It also can be implemented as part of smartphone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include one or more computer programs that are executable and/or interpretable on a programmable system. This includes at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a display device (e.g., a CRT (cathode ray tube) or LCD (liquid crystal display) monitor) for presenting data to the user, and a keyboard and a pointing device (e.g., a mouse or a trackball) by which the user can provide input to the computer. Other kinds of devices can be used to provide for interaction with a user as well. For example, feedback provided to the user can be a form of sensory feedback (e.g., visual feedback, auditory feedback, or tactile feedback). Input from the user can be received in a form, including acoustic, speech, or tactile input.

The systems and techniques described here can be implemented in a computing system that includes a backend component (e.g., as a data server), or that includes a middleware component (e.g., an application server), or that includes a frontend component (e.g., a client computer having a user interface or a Web browser through which a user can interact with an implementation of the systems and techniques described here), or a combination of such backend, middleware, or frontend components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the engines described herein can be separated, combined or incorporated into a single or combined engine. The engines depicted in the figures are not intended to limit the systems described here to the software architectures shown in the figures.

A number of embodiments of the invention have been described. Nevertheless, it will be understood that various modifications may be made without departing from the spirit and scope of the invention. For example, the system can have standard Helmholtz coils with different dimensions for generating a single axis, two-axis, or three-axis magnetic field. Accordingly, other embodiments are within the scope of the following claims.

What is claimed is:

1. A method comprising:
   receiving, at a magnetic sensor, a series of transmitter signals that are detected as a series of signals corresponding to different locations and/or orientations of a virtually-moving transmitter; and
   calculating, based at least on the received transmitter signals and a calibration matrix, one or both of an orientation matrix indicative of an orientation of the magnetic sensor relative to the virtually-moving transmitter and a positional matrix indicative of a position of the magnetic sensor relative to the virtually-moving transmitter,
wherein the series of transmitter signals are transmitted from the same physical location.

2. The method of claim 1, wherein three positional indicator values represent an x component, a y component, and a z component of the position of the magnetic sensor relative to the virtually-moving transmitter.

3. The method of claim 1, further comprising:
comparing the calculated orientation matrix and the positional matrix with theoretical values of orientation and position; and
determining whether the transmitter signals represent reliable orientation and positional information based on whether a difference between the values is within respective thresholds.

4. The method of claim 1, wherein the transmitter signals comprise a voltage signal generated based on interaction between the magnetic sensor and the magnetic field provided by the virtually-moving transmitter.

5. The method of claim 4, wherein values of voltages are indicative of the orientation and position of the magnetic sensor relative to the virtually-moving transmitter.

6. The method of claim 1, wherein the magnetic sensor is a three-axis sensor that includes a concentric, collocated set of sensor coils.

7. The method of claim 1, wherein the virtually-moving transmitter is a three-axis Helmholtz set of coils.

8. A non-transitory computer-readable medium comprising instructions that when executed by a processor perform a method comprising:
receiving, at a magnetic sensor, a series of transmitter signals that are detected as a series of signals corresponding to different locations and/or orientations of a virtually-moving transmitter; and
calculating, based at least on the received transmitter signals and a calibration matrix, one or both of an orientation matrix indicative of an orientation of the magnetic sensor relative to the virtually-moving transmitter and a positional matrix indicative of a position of the magnetic sensor relative to the virtually-moving transmitter,
wherein the series of transmitter signals are transmitted from the same physical location.

9. The computer-readable medium of claim 8, wherein three positional indicator values represent an x component, a y component, and a z component of the position of the magnetic sensor relative to the virtually-moving transmitter.

10. The computer-readable medium of claim 8, wherein the method comprises:
comparing the calculated orientation matrix and the positional matrix with theoretical values of orientation and position; and
determining whether the transmitter signals represent reliable orientation and positional information based on whether a difference between the values is within respective thresholds.

11. The computer-readable medium of claim 8, wherein the transmitter signals comprise a voltage signal generated based on interaction between the magnetic sensor and the magnetic field provided by the virtually-moving transmitter.

12. The computer-readable medium of claim 11, wherein values of voltages are indicative of the orientation and position of the magnetic sensor relative to the virtually-moving transmitter.

13. The computer-readable medium of claim 8, wherein the magnetic sensor is a three-axis sensor that includes a concentric, collocated set of sensor coils.

14. The computer-readable medium of claim 8, wherein the virtually-moving transmitter is a three-axis Helmholtz set of coils.

15. A system comprising:
a virtually-moving transmitter configured to generate a magnetic field;
a magnetic sensor configured to detect the generated magnetic field; and
a computing device in communication with the virtually-moving transmitter and the magnetic sensor, the computing device configured to:
receive, at a magnetic sensor, a series of transmitter signals that are detected as a series of signals corresponding to different locations and/or orientations of the virtually-moving transmitter; and
calculate, based at least on the received transmitter signals and a calibration matrix, one or both of an orientation matrix indicative of an orientation of the magnetic sensor relative to the virtually-moving transmitter and a positional matrix indicative of a position of the magnetic sensor relative to the virtually-moving transmitter,
wherein the series of transmitter signals are transmitted from the same physical location.

16. The system of claim 15, wherein three positional indicator values represent an x component, a y component, and a z component of the position of the magnetic sensor relative to the virtually-moving transmitter.

17. The system of claim 15, wherein the computing device is configured to:
compare the calculated orientation matrix and the positional matrix with theoretical values of orientation and position; and
determine whether the transmitter signals represent reliable orientation and positional information based on whether a difference between the values is within respective thresholds.

18. The system of claim 15, wherein the transmitter signals comprise a voltage signal generated based on interaction between the magnetic sensor and the magnetic field provided by the virtually-moving transmitter.

19. The system of claim 18, wherein values of voltages are indicative of the orientation and position of the magnetic sensor relative to the virtually-moving transmitter.

20. The system of claim 15, wherein the magnetic sensor is a three-axis sensor that includes a concentric, collocated set of sensor coils.

21. The system of claim 15, wherein the virtually-moving transmitter is a three-axis Helmholtz set of coils.

* * * * *